(12) United States Patent
Fermann et al.

(10) Patent No.: US 8,237,122 B2
(45) Date of Patent: Aug. 7, 2012

(54) OPTICAL SCANNING AND IMAGING SYSTEMS BASED ON DUAL PULSED LASER SYSTEMS

(75) Inventors: Martin E. Fermann, Dexter, MI (US); Ingmar Hartl, Ann Arbor, MI (US)

(73) Assignee: Imra America, Inc., Ann Arbor, MI (US)

( * ) Notice: Subject to any disclaimer, the term of this patent is extended or adjusted under 35 U.S.C. 154(b) by 0 days.

(21) Appl. No.: 13/399,392

(22) Filed: Feb. 17, 2012

(65) Prior Publication Data
US 2012/0145902 A1 Jun. 14, 2012

Related U.S. Application Data

(62) Division of application No. 12/399,435, filed on Mar. 6, 2009, now Pat. No. 8,120,778.

(51) Int. Cl.
*G01J 5/02* (2006.01)
(52) U.S. Cl. .................................................. 250/341.1
(58) Field of Classification Search ................. 250/341.1
See application file for complete search history.

(56) References Cited

U.S. PATENT DOCUMENTS

| | | | |
|---|---|---|---|
| 4,191,473 A | 3/1980 | Hansch |
| 4,451,923 A | 5/1984 | Hansch |
| 4,700,150 A | 10/1987 | Hall |
| 5,079,444 A | 1/1992 | Kallenbach |
| 5,359,612 A | 10/1994 | Dennis |
| 5,379,309 A | 1/1995 | Logan |
| 5,748,309 A | 5/1998 | van der Weide |
| 5,778,016 A | 7/1998 | Sucha |
| 6,038,055 A | 3/2000 | Hansch |
| 6,072,811 A | 6/2000 | Fermann |
| 6,192,058 B1 | 2/2001 | Abeles |
| 6,373,867 B1 | 4/2002 | Lin |

(Continued)

FOREIGN PATENT DOCUMENTS

DE 8026484 A1 12/2009

(Continued)

OTHER PUBLICATIONS

Apolonski A., et al., Controlling the Phase Evolution of Few-Cycle Light Pulses, Physical Review Letters, Jul. 24, 2000, vol. 85, No. 4, pp. 740-743.

(Continued)

*Primary Examiner* — David Porta
*Assistant Examiner* — Marcus Taningco
(74) *Attorney, Agent, or Firm* — Sughrue Mion, PLLC

(57) ABSTRACT

The invention relates to scanning pulsed laser systems for optical imaging. Coherent dual scanning laser systems (CDSL) are disclosed and some applications thereof. Various alternatives for implementation are illustrated, including highly integrated configurations. In at least one embodiment a coherent dual scanning laser system (CDSL) includes two passively modelocked fiber oscillators. The oscillators are configured to operate at slightly different repetition rates, such that a difference $\delta f_r$ in repetition rates is small compared to the values $f_{r1}$ and $f_{r2}$ of the repetition rates of the oscillators. The CDSL system also includes a non-linear frequency conversion section optically connected to each oscillator. The section includes a non-linear optical element generating a frequency converted spectral output having a spectral bandwidth and a frequency comb comprising harmonics of the oscillator repetition rates. A CDSL may be arranged in an imaging system for one or more of optical imaging, microscopy, micro-spectroscopy and/or THz imaging.

2 Claims, 10 Drawing Sheets

U.S. PATENT DOCUMENTS

| | | |
|---|---|---|
| 6,396,856 B1 | 5/2002 | Sucha |
| 6,570,704 B2 | 5/2003 | Palese |
| 6,590,910 B2 | 7/2003 | Lin |
| 6,654,394 B1 | 11/2003 | Sellin |
| 6,724,788 B1 | 4/2004 | Holzwarth |
| 6,751,385 B2 | 6/2004 | Futami |
| 6,785,303 B1 | 8/2004 | Holzwarth |
| 6,813,429 B2 | 11/2004 | Price |
| 6,813,447 B2 | 11/2004 | Ellis |
| 6,814,376 B2 | 11/2004 | Yu |
| 6,819,690 B2 | 11/2004 | Kartner |
| 6,885,683 B1 | 4/2005 | Fermann |
| 6,897,959 B2 | 5/2005 | Haensch |
| 7,026,594 B2 | 4/2006 | Holzwarth |
| 7,190,705 B2 | 3/2007 | Fermann |
| 7,202,993 B2 | 4/2007 | Tauser |
| 7,203,402 B2 | 4/2007 | Haensch |
| 7,218,443 B2 | 5/2007 | Tauser |
| 7,224,518 B2 | 5/2007 | Tauser |
| 7,414,780 B2 | 8/2008 | Fermann |
| 7,418,017 B2 | 8/2008 | Holzwarth |
| 7,450,813 B2 | 11/2008 | Dong |
| 7,496,260 B2 | 2/2009 | Dong |
| 7,672,342 B2 | 3/2010 | Gohle |
| 7,728,317 B2 | 6/2010 | Dilhaire |
| 7,804,863 B2 | 9/2010 | Adel |
| 7,809,222 B2 | 10/2010 | Hartl |
| 2004/0057682 A1 | 3/2004 | Nicholson |
| 2004/0190119 A1 | 9/2004 | Tauser |
| 2004/0213302 A1 | 10/2004 | Fermann |
| 2005/0047739 A1 | 3/2005 | Parker |
| 2005/0063425 A1 | 3/2005 | Krastev |
| 2005/0073689 A1 | 4/2005 | Pang |
| 2005/0169324 A1 | 8/2005 | Ilday |
| 2006/0268949 A1 | 11/2006 | Gohle |
| 2007/0086713 A1 | 4/2007 | Ingmar |
| 2008/0043784 A1* | 2/2008 | Wilcox .................. 372/18 |
| 2008/0069159 A1 | 3/2008 | Adel |
| 2008/0165355 A1* | 7/2008 | Yasui et al. .................. 356/323 |
| 2008/0179528 A1* | 7/2008 | Demers .................. 250/341.1 |
| 2009/0213880 A1 | 8/2009 | Ouchi |
| 2009/0296197 A1 | 12/2009 | Holzwarth |
| 2010/0225897 A1 | 9/2010 | Fermann |
| 2010/0265972 A1 | 10/2010 | Hartl |
| 2011/0019267 A1 | 1/2011 | Li |
| 2011/0069309 A1 | 3/2011 | Newbury |
| 2011/0141540 A1 | 6/2011 | Hochrein |

FOREIGN PATENT DOCUMENTS

| | | |
|---|---|---|
| JP | 2003-185626 A | 7/2003 |
| WO | WO 0221644 A2 | 3/2002 |
| WO | WO 2004077142 A1 | 9/2004 |
| WO | WO 2007/079342 A | 7/2007 |
| WO | WO 2009000079 A1 | 12/2008 |
| WO | WO 2009146671 A1 | 12/2009 |
| WO | WO 2010010437 A1 | 1/2010 |
| WO | WO 2010010438 A2 | 1/2010 |
| WO | WO 2010010444 A1 | 1/2010 |

OTHER PUBLICATIONS

Bartels A. et al: "Ultrafast time-domain 1 spectroscopy based on high-speed asynchronous optical sampling" Rev.of Sci. Instruments, AIP, vol. 78, No. 3, Mar. 22, 2007, pp. 35107-35107.

Bartels A., et al., Broadband phase-coherent optical frequency synthesis with actively linked Ti:sapphire and Cr:forsterite femtosecond lasers, Opt. Lett. 29, 403-405. (2004).

Bhushan A. S. et al., 150 Gsample/s wavelength division sampler with time-stretched output, Electron. Lett., vol. 34, No. 5, pp. 474475, 1998.

Chinese Office Action corresponding to Chinese Patent Application No. 2007-101533662 dated Jan. 8, 2010.

Cundiff S. et al., Femtosecond combs linewidth due to pulse dynamics in mode-locked laser, ThD4, pp. 719-720 Lasers and Electro-Optics Society, 2007. LEOS 2007. The 20th Annual Meeting of the IEEE.

Cundiff S., Colloquium: Femtosecond optical frequency combs, Review of Modern Physics, vol. 75, p. 325-342 (Jan. 1, 2003).

Diddam S. et al., An Optical Clock Based on a Single Trapped 199Hg+ Ion, Science 2001 293: 825-82.

Diddam S. et al., Direct RF of optical frequency measurements with a Femtosecond laser comb, IEEE Transactions on Intrumentation and Measurement, vol. 50, Is.2, p. 552-555 (Apr. 1, 2001).

E. Ebendorff-Heidepriem et al., Highly nonlinear bismuth-oxide-based glass holey fiber, presented at OFC 2004, Los Angeles, California, paper ThA4.

F. Fatemi, Frequency comb linewidth of an actively mode-locked fiber laser, Optical Society of America, Optics Letters, vol. 29, Issue 9, pp. 944-946 (2004).

I. Coddington et al., "Coherent Multiheterodyne Spectroscopy Using Stabilized Optical Frequency Combs," Phys. Rev. Lett. 100, 13902 (2008).

J. Mandon et al., "Fourier transform spectroscopy with a laser frequency comb", Nature Photonics, 3, 99-102, Jan. 25, 2009.

K. Holman, Detailed studies and control of intensity-related dynamics of femtosecond frequency combs from mode-locked Ti: Sapphire Lasers, IEEE J. of Sel. Topics in Quan. Electronics, vol. 9, Is. 4, p. 1018-1024 (Jul. 1, 2003).

Keilmann et al., "Time domain mid-infrared frequency-comb spectrometer", Opt. Lett., vol. 29, pp. 1542-1544 (2004),.

N. Newbury et al., "Low-noise fiber-laser frequency combs," Journal of the Optical Society of America B 24, 1756-1770 (2007).

P. Giaccari et al., "Active Fourier-transform spectroscopy combining the direct RF beating of two fiber-based mode-locked lasers with a novel referencing method", Opt. Express., vol. 16, pp. 4347 (2008).

Poppe, Few-cycle optical waveform synthesis, Appl. Phys. B Lasers Opt. 72,977.

R. Jason Jones et al., "Stabilization of Femtosecond Lasers for Optical Frequency Metrology and Direct Optical to RadioSynthesis" PRL 86, p. 3288 (2001).

S. Diddams et al., A phase and frequency controlled femtosecond laser for metrology and single-cycle nonlinear optics ASSL 2000 p. 631-633.

T.W. Hansch et al., Laser frequency stabilization by polarization spectroscopy of a reflecting reference cavity, Optics Communications, vol. 35, Issue 3, Dec. 1980, pp. 441-444.

Telle, Carrier-envelope offset phase control Appl. Phys. B 69, 327 (1999).

Udem, "Chapter 8" from Dissertation (in German) LMU 1997 "Phasenkoharente optiche Frequenzmessungen am Wasserstoffatom. Bestimmung der Rydberg-Konstanten und der 1S Lambe-Verschiebung".

Xu et al, "Route to phase control of ultrashort light pulses", Optics Letters, vol. 21, Issue 24, pp. 2008-2010 (1996).

Yasui et al., "Terahertz frequency comb by multifrequency-heterodyning photoconductive detection for high-accuracy, high-resolution terahertz spectroscopy", Appl. Phys. Lett., vol. 88, pp. 211104-1 to 211104-3 (2006).

* cited by examiner

OPTICAL SCANNING AND IMAGING SYSTEMS BASED ON DUAL PULSED LASER SYSTEMS

CROSS-REFERENCE TO RELATED APPLICATION

This application is a divisional of U.S. application Ser. No. 12/399,435 filed Mar. 6, 2009, the disclosure of which is incorporated herein by reference in its entirety.

BACKGROUND OF THE INVENTION

1. Field of the Invention

The invention relates to scanning pulsed laser systems for optical imaging.

2. Description of the Related Art

Dual pulsed laser systems comprising two modelocked lasers operating at two slightly different repetition rates $f_1$ and $f_2$, such that $\delta = |(f_1-f_2)| \ll f_1$ and $\delta = |(f_1-f_2)| \ll f_2$, are useful instruments for the rapid interrogation of optical response functions of widely varying electronic and opto-electronic devices such as photoconductive switches and integrated circuits. Additionally the use of dual pulsed laser systems has also been suggested for THz imaging as disclosed in U.S. Pat. No. 5,778,016 and U.S. Pat. No. 6,396,856 to Sucha et al.

The use of dual modelocked lasers can be replaced for probing the optical response functions by implementing dual electronic circuit systems, as has been suggested in U.S. Pat. No. 5,748,309 by van der Weide. The approach has some benefit for the interrogation of the spectral dependence of signal transmission in the THz spectral range. Two pulsed signal sources also operating at two slightly different repetition rates $f_1$ and $f_2$ were disclosed, which produce emission in the THz spectral range made up of frequency lines comprising pure harmonics of the two repetition rates. Detection of the beat signal at $\delta, 2\delta, \ldots n\delta$ is then used to infer the signal transmission at the harmonics of the repetition rate $f_1$, $2f_1, \ldots nf_1$. Note that in this scheme a beat signal at a difference frequency as low as $\delta$ is used, which is not ideal, since $\delta$ typically has a small value where acoustic noise can corrupt the signal.

The use of mode locked lasers was again later disclosed by Keilmann et al., in 'Time domain mid-infrared frequency-comb spectrometer', Opt. Lett., vol. 29, pp. 1542-1544 (2004), who suggested the use of a dual scanning laser system for Fourier Transform Spectroscopy (FTS) and the analysis of the spectral transmission of materials in the infrared spectral range.

In order to improve the scan rate of dual laser scanning FTS, Keilmann et al., in International Patent Application Publication WO2007/045461, further suggested to dither the repetition rate of one laser versus the other using techniques similar to the ones described in the '016 patent.

The use of lasers for spectroscopy has also been suggested by Haensch et al. in U.S. Pat. No. 7,203,402, where a single frequency comb laser based on a mode-locked laser was used for the measurement of certain properties of optical elements. Here the measurement was performed either simultaneously or sequentially at each individual frequency line of the comb laser.

A frequency comb laser was recently also combined with a conventional Fourier transform spectrometer to obtain an improved signal/noise ratio for spectral measurements (J. Mandon et al., 'Fourier transform spectroscopy with a laser frequency comb', in Nature Photonics, 2009)

Prior dual scanning laser systems have a number of limitations when applied to spectroscopy. The low repetition rate of implemented laser sources leads to excessively long data acquisition times. and the techniques for signal generation in the near IR to mid-IR spectral range are relatively cumbersome. Systems implemented with bulky solid-state lasers are not well suited for instrumentation applications and require a large components count. Other systems (P. Giaccari et al., 'Active Fourier-transform spectroscopy combining the direct RF beating of two fiber-based mode-locked lasers with a novel referencing method', Opt. Express., vol. 16, pp. 4347 (2008)) and (I. Coddington et al., "Coherent Multiheterodyne Spectroscopy Using Stabilized Optical Frequency Combs," Phys. Rev. Lett. 100, 13902 (2008)) provide only very limited spectral coverage.

SUMMARY OF THE INVENTION

In the following we refer to dual scanning laser systems that exploit the discrete frequency spectrum, i.e. the comb spectrum, of modelocked lasers but that do not require or do not rely on precision comb control inside the laser oscillator as coherent dual scanning lasers, CDSLs.

Here we disclose a new CDSL for applications in spectroscopy, micro-spectroscopy, microscopy, Fourier transform spectroscopy (FTS), optical and THz imaging, and/or similar applications. The CDSLs are based on modelocked fiber lasers designed for operation at high repetition rates allowing for large scanning speeds. Efficient spectroscopic measurements are enabled by the implementation of low noise, phase controlled fiber lasers, which are designed to provide broad spectral coverage via the implementation of nonlinear spectrally broadening optical elements. Various compact designs are described. In various embodiments a reduction of component count is further accomplished via simultaneous use of nonlinear spectral broadening elements and the use of appropriate time delays between the lasers.

We further disclose the use of highly nonlinear waveguides in conjunction with coherent supercontinuum generation for generating an optical output from the visible to the mid-infrared spectral region. Difference frequency generation (DFG) produces output in the mid-IR spectral region and simplifies the implementation of FTS. DFG eliminates variations of the carrier envelope offset frequency external to the laser cavity and thus produces an output spectrum comprising true harmonics of the laser repetition rates.

In conjunction with photoconductive antennas spectral emission in the THz spectral region can be obtained.

In order to use difference frequency generation effectively, the mode locked lasers can be configured with two outputs each. Amplifiers can be further implemented to amplify those outputs. Supercontinuum generation can then be implemented for spectral broadening of these fiber laser outputs. Difference frequency generation can be implemented between spectral components of the supercontinuum or between a spectral component of the supercontinuum and another fiber laser output.

Nonlinear signal interference in nonlinear frequency broadening elements from overlapping pulses can be eliminated by using separate nonlinear frequency broadening elements for each laser. Alternatively, an optical delay line can be inserted at the output of the CDSL to produce an interference signal only from pulses that do not overlap in any nonlinear optical elements. Electronic gating can further be implemented for optimum signal conditioning.

In at least one embodiment the carrier envelope offset frequencies in coherent dual scanning femtosecond modelocked fiber lasers can be adjusted by control of various intra-cavity optical elements such as intra-cavity loss, saturable absorber temperature, fiber temperature and fiber grating temperature. In some embodiments carrier envelope offset frequency control can be averted by the implementation of DFG.

In at least one embodiment the carrier envelope offset frequencies and repetition rates in coherent dual scanning femtosecond modelocked fiber lasers can further be controlled by phase locking the two lasers to external cavities.

In at least one embodiment the carrier envelope offset frequencies and repetition rates in coherent dual scanning femtosecond modelocked fiber lasers can further be controlled by phase locking the two lasers to two external single-frequency lasers.

In another embodiment the difference in carrier envelope offset frequencies and the repetition rates in coherent dual scanning femtosecond modelocked fiber lasers can further be controlled by phase locking the two lasers to one external single-frequency laser.

For improved spectral resolution coherent dual scanning femtosecond modelocked fiber lasers can also be constructed with lasers where the repetition rate of one laser is an approximate harmonic of the repetition rate of the other laser.

The noise of the carrier envelope offset frequencies can be minimized by an appropriate adjustment of the intra-cavity laser dispersion, and the pulse width injected into the supercontinuum fibers.

Any drift in carrier envelope offset frequency between the two lasers in the CDSLs can be monitored and corrected for by external optical means. Also, an f–2f interferometer can be implemented for carrier envelope offset frequency monitoring.

DETAILED DESCRIPTION OF THE INVENTION

Figure 1:
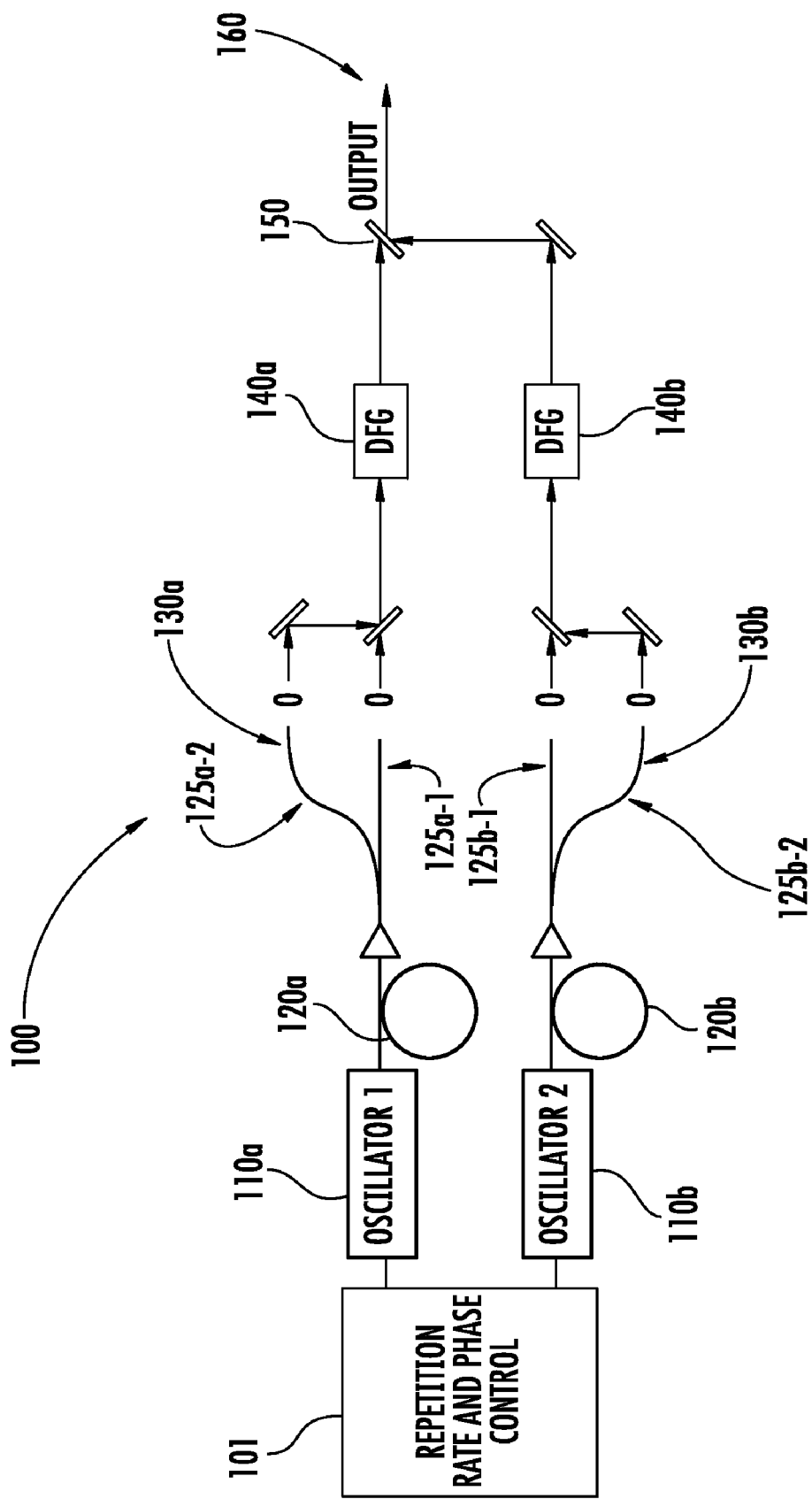
FIG. 1 is a diagram illustrating an example of a CDSL.

This description first discusses some aspects of modelocked lasers and frequency comb generation particularly related to CDSL and applications thereof. Examples of applications of such lasers for IR spectroscopy and THz imaging are included.

Modelocked lasers with fixed optical frequency spectra comprising a set of equidistant optical frequency lines are typically also referred to as frequency comb lasers. The optical frequency spectrum of a frequency comb laser can be described by $S(f) = f_{ceo} + mf_{rep}$, where m is an integer, $f_{ceo}$ is the carrier envelope offset frequency and $f_{rep}$ is the repetition rate of the laser. The amplitudes of the individual frequency lines in fact sample the optical envelope spectrum at discrete points $f_{ceo} + mf_{rep}$ in optical frequency space.

Frequency comb lasers were described in U.S. Pat. No. 6,785,303 to Holzwarth et al., where the control of the pump power of a modelocked laser in conjunction with electronic feedback loops is used to stabilize $f_{ceo}$ and thereby to stabilize the location of all individual frequency lines that comprise the optical frequency spectrum. In a standard modelocked laser $f_{ceo}$ is not controlled and therefore only the separation of all individual frequency lines is stable, apart from a slow drift of $f_r$ due to cavity length fluctuations. As disclosed above the spectral separation corresponds to the repetition rate $f_{rep}$ of the modelocked oscillator, which is generally a frequency in the MHz regime, and in various embodiments described herein more preferably about 1 GHz or even higher. The exact location of the lines inside the frequency spectrum varies randomly. However, the optical spectrum of a frequency comb laser and a modelocked laser can have the same envelope function. Also even if $f_{ceo}$ is not controlled, the optical spectrum of a modelocked laser comprises a number of discrete frequency lines.

When operating two frequency comb lasers at slightly different repetition rates $f_{rep}$ and $f_{rep} + \delta$ respectively, and when overlapping the output of the two lasers on a detector various beat frequencies can be observed in the RF domain. When further ensuring that for both lasers frequency teeth of order m are the most proximate, the RF spectrum includes harmonic frequencies $m\delta + \Delta f_{ceo}$, $(m+1)\delta + \Delta f_{ceo}$, $(m+2)\delta + \Delta f_{ceo}$ ... with amplitudes from the geometrical mean of the amplitudes at optical frequencies $mf + f_{ceo1}$ and $m(f+\delta) + f_{ceo2}$ where $\Delta f_{ceo} = f_{ceo1} - f_{ceo2}$. The parameter $f_{rep}/\delta$ is the scaling factor that scales the RF frequencies to the optical frequencies. For example for $\delta = 10$ Hz and $f_{rep} = 1$ GHz, we obtain a scaling factor of $10^8$; an intensity measured in the RF domain at 1 MHz corresponds to an optical frequency of $10^{14}$ Hz. $\Delta f_{ceo}$ can be selected to further lower the RF frequency where measurements need to be performed in order to obtain the amplitude of the optical frequencies. The RF frequency at which measurements are to be performed can be changed by ensuring that for the two lasers frequency teeth of order m and n respectively are most proximate. In this case the beat frequencies are given by $(m-n)f_r+m\delta+\Delta f_{ceo}$; $(m-n)f_r+(m+1)\delta+\Delta f_{ceo}$; $(m-n)f_r+(m+2)\delta+\Delta f_{ceo}$ ....

The need for a comb laser with a fixed optical frequency spectrum for spectroscopic measurements can be relaxed via the implementation of correction techniques that monitor the drift of the frequency lines within the spectral envelope, as recently discussed by P. Giaccari et al., 'Active Fourier-transform spectroscopy combining the direct RF beating of two fiber-based mode-locked lasers with a novel referencing method', Opt. Express., vol. 16, pp. 4347 (2008).

Alternatively, the drift of the individual frequency lines can be eliminated by adding a nonlinear frequency conversion section after a modelocked oscillator. For example when implementing difference frequency generation between the red and blue part of the modelocked laser spectrum, it is well known that the individual frequency lines occur precisely at true harmonics of the laser repetition rate independent of the value of $f_{ceo}$. As previously discussed, we refer to dual scanning laser systems that take advantage of the discrete frequency spectrum of modelocked lasers but that do not rely on precision phase or $f_{ceo}$ control inside the laser oscillator generally as CDSLs.

For any instrumentation applications of modelocked lasers, mode-locked fiber lasers have several advantages over both mode-locked bulk solid state lasers and mode-locked diode lasers. Mode-locked fiber lasers offer typically superior noise properties compared to mode-locked diode lasers and can be packaged in smaller spaces than mode-locked bulk solid state lasers. Mode-locked fiber lasers can be produced with excellent thermal and mechanical stability. Passively mode-locked fiber lasers in particular can be constructed with few and inexpensive optical components, suitable for mass production, as disclosed in U.S. Pat. No. 7,190,705 to Fermann et al. and Ser. No. 11/546,998 to Hartl et al. U.S. Pat. No. 7,190,705 is hereby incorporated by reference in its entirety. Additionally, the use of dual pulsed laser systems has also been suggested in THz imaging as disclosed in U.S. Pat. No. 5,778,016 and U.S. Pat. No. 6,396,856 to Sucha et al. The '016 and '856 patents also disclose various techniques and configurations for controlling relative and absolute timing drift of mode-locked lasers. U.S. Pat. Nos. 5,778,016 and 6,396,856 are hereby incorporated by reference in their entirety.

The dispersion compensated fiber lasers as disclosed in '705 provide for the construction of low noise frequency comb sources. Also disclosed were designs of fiber lasers operating at repetition rates in excess of 1 GHz.

Low-noise operation of fiber lasers minimizes their timing jitter, allowing optimized control of the timing of the pulses. The '705 patent disclosed the first low noise fiber-based frequency comb source. Low noise operation was obtained by controlling the fiber cavity dispersion in a certain well-defined range. Low noise operation of fiber frequency comb sources is generally required in order to minimize the noise of the carrier envelope offset frequency $f_{ceo}$ of the laser to a negligible level, and also to facilitate measurement and control of $f_{ceo}$.

Some examples of fiber-based CDSL systems are disclosed below. Implementations providing for high repetition rate, low-noise, and a high-level of integration are described. Non-linear spectral generation and various implementations for phase-control lead to stable output signals in the near-IR range, thereby providing benefits for IR spectroscopy and THz imaging applications.

FIG. 1 schematically illustrates a coherent dual scanning laser system 100 (CDSL) according to an embodiment. In this example two mode-locked oscillators 110a, 110b having slightly different repetition rates are utilized to provide input pulse trains. A pulse train from each oscillator is amplified and split into first and second optical paths. The pulses in each path are conditioned with a dispersion compensator. An intermediate non-linear frequency conversion section generates a supercontinuum along a first path, which is then combined with the pulse train in the second path using a non-linear frequency converters for DFG. The DFG outputs corresponding to each of the oscillators 110a, 110b are then combined to produce CDSL output.

Referring to FIG. 1, the system comprises two oscillators 110a-, 110-b (oscillator 1 and oscillator 2), which preferably generate pulses that can be compressed to the femtosecond (fs) time scale. Preferably oscillators 110a,110b are implemented using Er, Yb or Tm oscillators operating at repetition rates of about 250 MHz or higher. Such oscillators were for example described in U.S. Pat. No. 7,190,705 to Fermann et al. and Ser. No. 11/546,998 to Hartl et al. as well as in U.S. provisional application U.S. 61/120,022, entitled "Highly Rare-Earth-Doped Optical Fibers for Fiber Lasers and Amplifiers" to Dong et al., which is incorporated herein by reference. Various examples disclosed in the '022 application include highly rare earth doped gain fibers having pump absorption of up to about 5000 dB/m, and gain per unit length in the range of 0.5-5 dB/cm. Various dopant concentrations reduce Yb clustering thereby providing for high pump absorption, large gain, with low photodarkening. Such rare-earth doped fibers provide for construction of short cavity length fiber lasers, and for generation of high energy ultrashort pulses at a repetition rate exceeding 1 GHz. Such configurations provide for high signal to noise operation of CDSLs. By way of example, other fiber configurations having high pump absorption compared to conventional silica fibers, for example absorption of 300-1500 dB/m at 976 nm are also disclosed in U.S. Ser. No. 11/693,633, entitled "Rare earth doped and large effective area optical fibers for fiber lasers and amplifiers", now published as U.S. patent application pub. no. 2008/0069508. U.S. Ser. No. 11/693,633 is hereby incorporated by reference in its entirety.

The output of the oscillators is preferably passed through optical isolators (not shown) to minimize their sensitivity to backreflections. The repetition rates of the two oscillators can be monitored using two tab-couplers inserted into the output of the two oscillators, which direct a small fraction of the output of the oscillators onto two detectors (not shown), which provide signals representative of the repetition rate to controller 101.

The oscillators can be constructed to operate at respective repetition rates of f and $f+\delta$, where $\delta<<f$. Alternatively, the repetition rate of the second oscillator can be selected to be of +6, where n is an integer. The difference between their repetition rates $\delta$, or $(n-1)f+\delta$ for the case of widely dissimilar repetition rates, can then be controlled by repetition rate control element 101 comprising phase-locked loops and an intra-cavity transducer introduced into one of the oscillators. Such an intra-cavity transducer can be a mirror mounted on a piezoelectric element or a fiber heating element, for example as discussed in U.S. Pat. No. 7,190,705 to Fermann et al. and U.S. patent application Ser. No. 11/546,998 to Hartl et al. The oscillators may emit nearly chirp free pulses or slightly chirped pulses. Preferably any chirped pulses emitted from the oscillators 110-a,110-b have nearly-identical chirp. Preferably the power of both oscillators can be adjusted over some range, for example by a variable attenuator.

The outputs of the oscillators are coupled to two fiber amplifiers 120-a, 120-b. The fiber amplifiers are preferably cladding pumped. Such cladding pumped amplifiers are discussed in U.S. Pat. No. 7,190,705 to Fermann et al. Also cladding pumping via optical star-couplers as described by Dong et al. in Ser. No. 61/120,022 "Highly Rare-Earth-Doped Optical Fibers for Fiber Lasers and Amplifiers" can be implemented and is not further discussed here. Preferably the dispersion in both oscillators-amplifier propagation paths is matched.

In the example of FIG. 1 optical signal pulses output from each fiber amplifier are split into two arms: arms 125a-1, 125a-2 optically connected to amplifier 120a and oscillator 110a, and arms 125b-1, 125b-2 optically connected to amplifier 120b and oscillator 110b. Optical fiber couplers are preferred, and splitting ratios between 5/95 and 50/50 can be implemented. Each arm may be implemented in an all-fiber configuration as illustrated. In some embodiments at least a portion of an arm may be constructed with bulk components.

Dispersion compensation is carried out in the optical paths of each arm to compensate for dispersion, for example with a series of dispersion compensating elements forming a dispersion compensator. At least a portion of the arms may be constructed from identical components, including the various dispersion compensating elements. Dispersion compensating elements can include optical elements for pulse compression to provide high-quality femtosecond pulses, and may provide complete dispersion compensation or produce slightly negatively or positively chirped pulses at their output. When complete dispersion compensation is used, the output pulses are nearly transform limited.

A dispersion compensator can comprise several different fiber elements, and may be implemented with an integrated "all-fiber" design as will be further discussed below with respect to FIG. 2. For example, a first fiber element can comprise a positive dispersion fiber designed to spectrally broaden the output of the amplifier, and at least a second fiber element for dispersion compensation and for compressing the spectrally broadened output to near the bandwidth limit. Preferably the pulse compressing fiber element comprises a dispersion compensating fiber or a photonic crystal fiber with a central air-hole to minimize the nonlinearity of the dispersion compensation stage. Pulse compression via higher-order soliton compression in one or more negative dispersion fiber elements can be implemented. Also, bulk optic dispersion compensation elements such as grating, prism or grism pairs may be used. Preferably, the pulses are compressed to a pulse width less than about 500 fs, more preferably to a pulse width about less than 300 fs, and most preferably to a pulse width less than about 100 fs.

Optical pulses propagating in arms 125a-2, 125b-2 are also frequency converted in a non-linear frequency conversion section having frequency conversion elements 130a, 130b. Frequency conversion elements 130a, 130b can include optical elements for supercontinuum generation to provide pulses with a spectral bandwidth of at least a substantial fraction of an optical octave, and substantially broader than an output spectrum of oscillators 110a, 110b. Frequency conversion elements 130a,130b generate a broadband spectrum, for example a spectrum extending into the near mid-IR region, for example extending from the near IR to the range of at least about 3-5 μm, or up to about 10-20 μm.

In various implementations a frequency conversion section preferably comprises a highly nonlinear fiber, a periodically poled LiNbO3 (PPLN) waveguide, a silicon waveguide or any other suitable nonlinear waveguide. An element may also be optically patterned or periodically or aperiodically poled or have periodic variations of the $2^{nd}$-order nonlinearity along its length. The frequency conversion sections 130a, 130b in each arm generate an optical supercontinuum spectrum that can extend into the mid-IR when using highly nonlinear fluoride or chalcogenide waveguides. Supercontinuum generation in nonlinear waveguides was described in U.S. patent application Ser. No. 11/546,998 to Hartl et al. and is not further discussed here. As known in supercontinuum generation, the fundamental frequency comb structure from the oscillators is preserved. The additional spectral output generated comprises individual frequency teeth separated in frequency by the repetition rate of the laser. However, the injection of pulses shorter than 300 fs, and more preferably shorter than 100 fs, reduces the incoherent background between individual frequency teeth of the supercontinuum spectrum. The incoherent background is undesirable because it reduces the signal contrast in CDSLs. The influence of incoherent background noise to the comb contrast is described in N. Newbury and W. Swann, "Low-noise fiber-laser frequency combs," Journal of the Optical Society of America B 24, 1756-1770 (2007) which is incorporated herein by reference.

Difference frequency generation (DFG) is carried out in non-linear frequency conversion sections 140a,140b by mixing the dispersion compensated output signal pulses from paths 125a-1,125b-1 with the corresponding dispersion compensated and frequency converted outputs, including a supercontinuum generated in a section of arms 125a-2, 125b-2. The outputs are mixed in frequency converters 140a, 140b. Frequency converters 140a, 140b are preferably configured with nonlinear crystals such as $LiNbO_3$, GaAs, GaSe, GaP or any other suitable nonlinear crystal. These nonlinear crystals may also be periodically poled, optically patterned or have periodic variations of their $2^{nd}$ order nonlinearity along their length. Nonlinear waveguides can also be implemented. Frequency filters and polarization controllers can further be included upstream of DFG elements 140a, 140b and are not separately shown. The output from DFG elements is combined via beam splitter 150 and directed to the output 160.

In various embodiments the optical signal pulses output from the amplifiers are further directed through an optical isolator before injection into the dispersion compensation and frequency conversion stages. Appropriate time delays between the two oscillators are further introduced to ensure pulse overlap in the DFG elements and beam splitter 150. Such time delays can be introduced by well known methods of controlling the fiber lengths and free space propagation paths and are not separately shown here.

An all-fiber construction of a dispersion compensator and non-linear frequency section of each arm provides some benefits. One benefit of using a highly nonlinear fiber for frequency conversion sections 130a, 130b is that the amplifier stages 120a, 120b, the dispersion compensation elements and the frequency conversion section 130a, 130b can all be spliced together as schematically illustrated in FIG. 2. Various elements are shown in FIG. 2 which may be used in each arm, particularly in 125a-2,125-b2 where both dispersion compensation and super-continuum generation are performed. Polarization maintaining fiber components can also be implemented, or alternatively polarization controllers (not shown) can be used to optimize the polarization state for supercontinuum generation. A fiber pig-tailed isolator (not shown) preferably isolates the output of the amplifier from unwanted backreflections.

Figure 2:
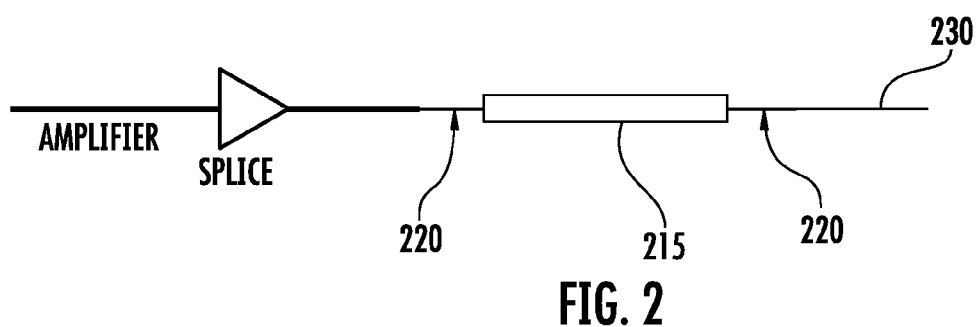
FIG. 2 is a schematic diagram of an optically integrated dispersion compensator, and non-linear frequency conversion section as used for supercontinuum generation.

In the example illustrated in FIG. 2, a dispersion compensation fiber 215 is spliced onto a length of transfer fiber 220 on each end, which transforms the fundamental mode of the fiber to match the mode in the adjacent fiber, such as any amplifiers 120a,120b providing inputs, or a highly nonlinear fiber 230 providing an output as shown in FIG. 2. The highly non-linear fiber, configured with the arrangement as shown in FIG. 2, may also be utilized in frequency conversion sections, for example sections 130a, 130b. A transfer fiber 220 can comprise more than one piece of fiber and can also comprise fiber optic tapers.

The output pulses of the amplifier emitted from transfer fiber 220 are then compressed in a length of dispersion compensation fiber 215. A length of photonic crystal fiber can be used, but any other type of fiber with suitable nonlinear and linear properties can also be implemented for pulse compression. Both linear and nonlinear amplifiers, such as similariton amplifiers as described in U.S. Pat. No. 6,885,683 to Fermann et al., can be implemented. When nonlinear amplifiers are implemented the oscillator power-levels can be preferably adjusted. For example similariton amplifiers produce positively chirped pulses, which can be compressed to near the bandwidth limit in a length of photonic crystal fiber as discussed in U.S. Pat. No. 7,414,780 to Fermann et al.

The highly nonlinear fiber 230 is then used for supercontinuum generation. Highly nonlinear fibers based on silica, are discussed in U.S. Pat. No. 7,496,260, entitled "Ultra High Numerical Aperture Optical Fibers" to Dong et al., which is hereby incorporated by reference in its entirety. In various embodiments non-silica-fibers with improved IR transparency can be used. For example nonlinear fluoride, bismuth, telluride or chalcogenide fibers can be implemented. Such IR transmitting fibers can transmit wavelengths up to around 20 μm and are commercially available. Because the melting temperature of mid-IR transmission fiber is typically much smaller than the melting temperature of silica fibers, optical lens arrangements can further be used to couple light from the dispersion compensating fiber to the highly nonlinear fiber in order to avoid complicated splicing of fibers with largely different melting temperatures.

Figure 3:
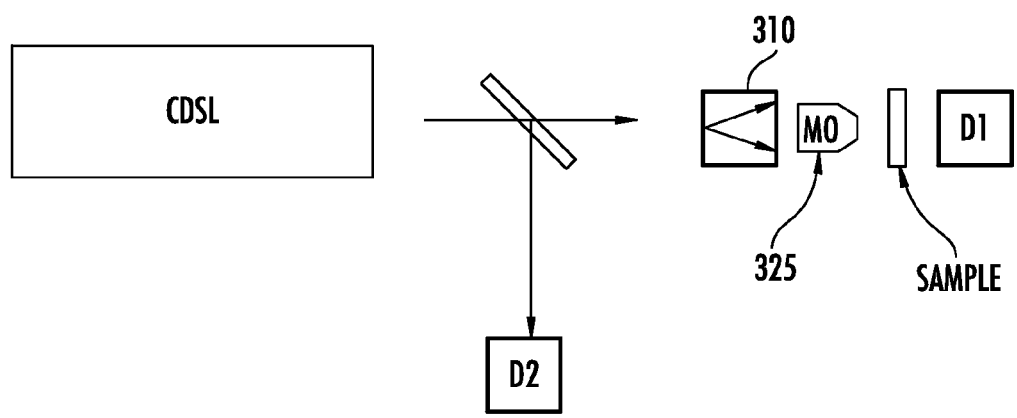
FIG. 3 is a schematic diagram of a CDSL as used for optical imaging applications.

An optical imaging system that includes a CDSL is shown in FIG. 3. Here a beam splitter is inserted after the output of the CDSL and splits the output along two optical paths. The beam splitter directs a fraction of the output along a first path onto detector D2, which is used to measure a reference spectrum, representing the output of the CDSL as a function of wavelength. The sample under test is inserted into the second path. By dividing the spectrum measured with detector D1 by the spectrum measured with detector D2 an accurate absorption spectrum of the test sample can be obtained. Such two detector schemes are well known in standard Fourier transform spectroscopy to eliminate spectral variations and temporal drifts of the light source in absorption measurements. In order to obtain the spatial distribution of the sample absorption and to perform imaging, an optical scanner 310 such as a commercially available galvanometer mirror system is further inserted into the second beam path of the output of the CDSL. In some embodiments the sample under test can be mounted on a movable stage. In various embodiments a combination of beam motion and movement of the sample may be utilized. The output of the CDSL is then focused onto the sample under test with a microscope objective 325 or other suitable beam delivery optics. The transmitted light is detected with a detector D1. In various embodiments one reference spectrum is obtained with detector D2. Alternatively, detector D2 can be omitted and the reference spectrum can be obtained by taking the sample out of the beam path 2. In some embodiments reflected light may be detected, or a combination of transmitted and reflected light. In order to improve the signal to noise ratio in the IR, cooling of the detector can also be implemented. For example liquid nitrogen cooled HgCdTe (MCT) detectors can be implemented that are commercially available with detection bandwidths up to 100 MHz. Also filter wheels (not shown) can be inserted anywhere in the beam path to select certain optical frequency ranges. An image is then obtained by monitoring RF spectra for each image point and by appropriately relating those RF spectra to optical transmission or reflection spectra.

The detector D1 monitors beat frequencies in the RF domain. Due to scaling of the optical frequencies to the RF frequencies with a scaling factor $f_{rep}/\delta$ in a CDSL we can interpret the function of the CDSL as representing a frequency grid in the RF domain for scaling RF to optical frequencies; each optical frequency is uniquely mapped onto an RF frequency, with a 1:1 correspondence. Difference frequency generation as illustrated in FIG. 1 cancels the carrier envelope offset frequencies external to the lasers. Because the carrier envelope offset frequencies of the two lasers after the DFG stages are zero, the relation between optical $f_{opt}$ and RF beat frequencies $f_{rf}$ is given by $$f_{opt} = f_{rf} \times f_{rep}/\delta \qquad (1),$$

where the minimum RF frequency $RF_{min}$ that contains information about signal transmission at optical frequencies is given by $m\delta$. Note that since m is a large number (of order $10^4$ or higher), $RF_{min}$ can be of the order of MHz.

Figure 4:
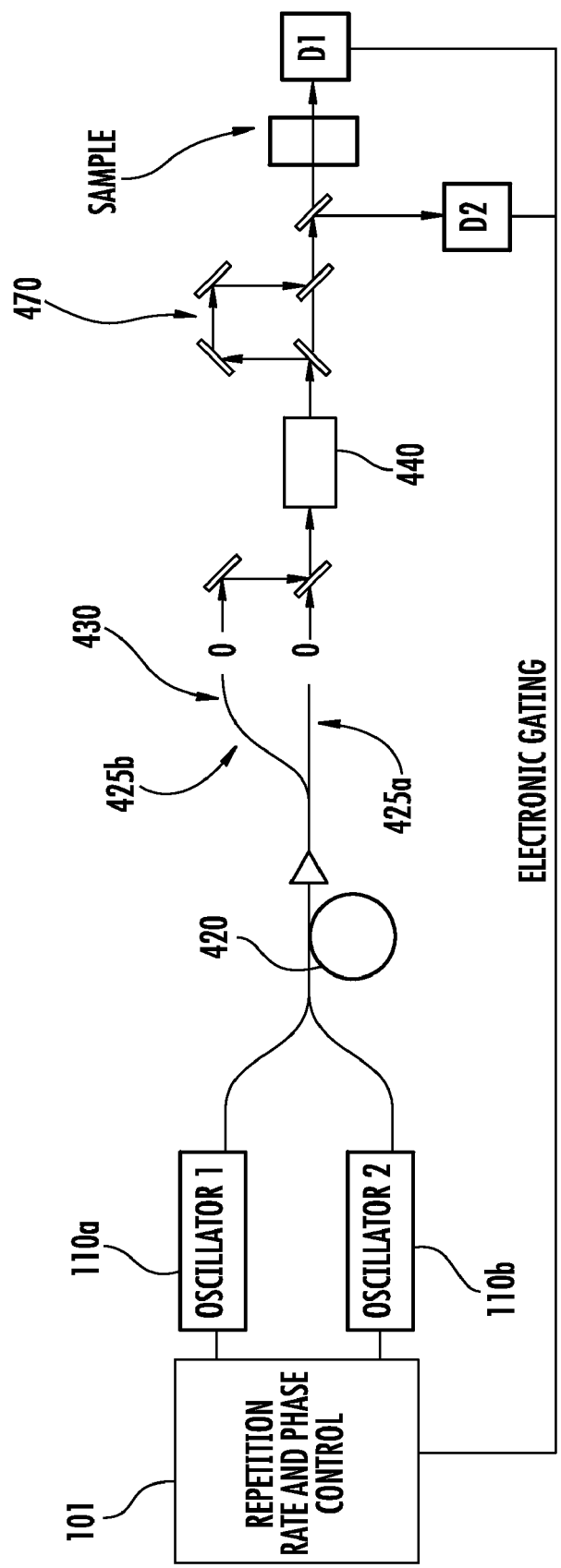
FIG. 4 is a schematic diagram of a CDSL designed with a reduced number of components.

An alternative embodiment of a CDSL is shown in FIG. 4. Here the component count is reduced by using two oscillators operating at slightly different repetition rates. The oscillator outputs are combined, and coupled into a common propagation path. The components in the common propagation path may be similar or identical to the ones described with respect to FIG. 1. In this example one amplifier 420, one intermediate supercontinuum generation section 430 and one DFG section 440 are used. The output of amplifier 420 is split into arms 425a, 425b in a manner similar to that illustrated in FIG. 1. DFG is obtained from mixing the dispersion compensated output of arm 425a with the output from the supercontinuum generator configured in arm 425b. Non-linear crystal 440 provides for DFG, as discussed with respect to FIG. 1. The output of the system is detected with detectors D1 and D2, where D2 is used to obtain a reference spectrum and D1 is used to measure the absorption of the test sample. Additional optical components for scanning can also be incorporated as in the example of FIG. 3.

In order to avoid signal degradation due to nonlinear interactions at times when the output pulses of the two oscillators overlap in time at the DFG section, the detectors can be electronically gated to be non-responsive at those times. In order to obtain an interference signal at times when the output pulses of the two oscillators do not overlap in time, an optical delay line 470 can be incorporated in front of the detector D1 and D2 (or at the output of the CDSL) as shown. In at least one embodiment a delay line based on a Mach-Zehnder interferometer is utilized, although other types of delay lines such as a Michelson interferometer with unbalanced arm lengths can also be implemented. The time delay line conveniently produces a time delay of a fraction of the cavity round trip time of the two lasers, where preferably this fraction is 50%. When recording an interferogram with an optical delay line a small penalty results from increased background signal and increased shot noise, but that penalty is greatly offset by the benefit of reduced component count of the system. Unwanted nonlinear pulse interactions due to potential pulse overlap in other parts of the system can be further avoided by an appropriate control of the pig-tail lengths from the two oscillators.

Figure 5:
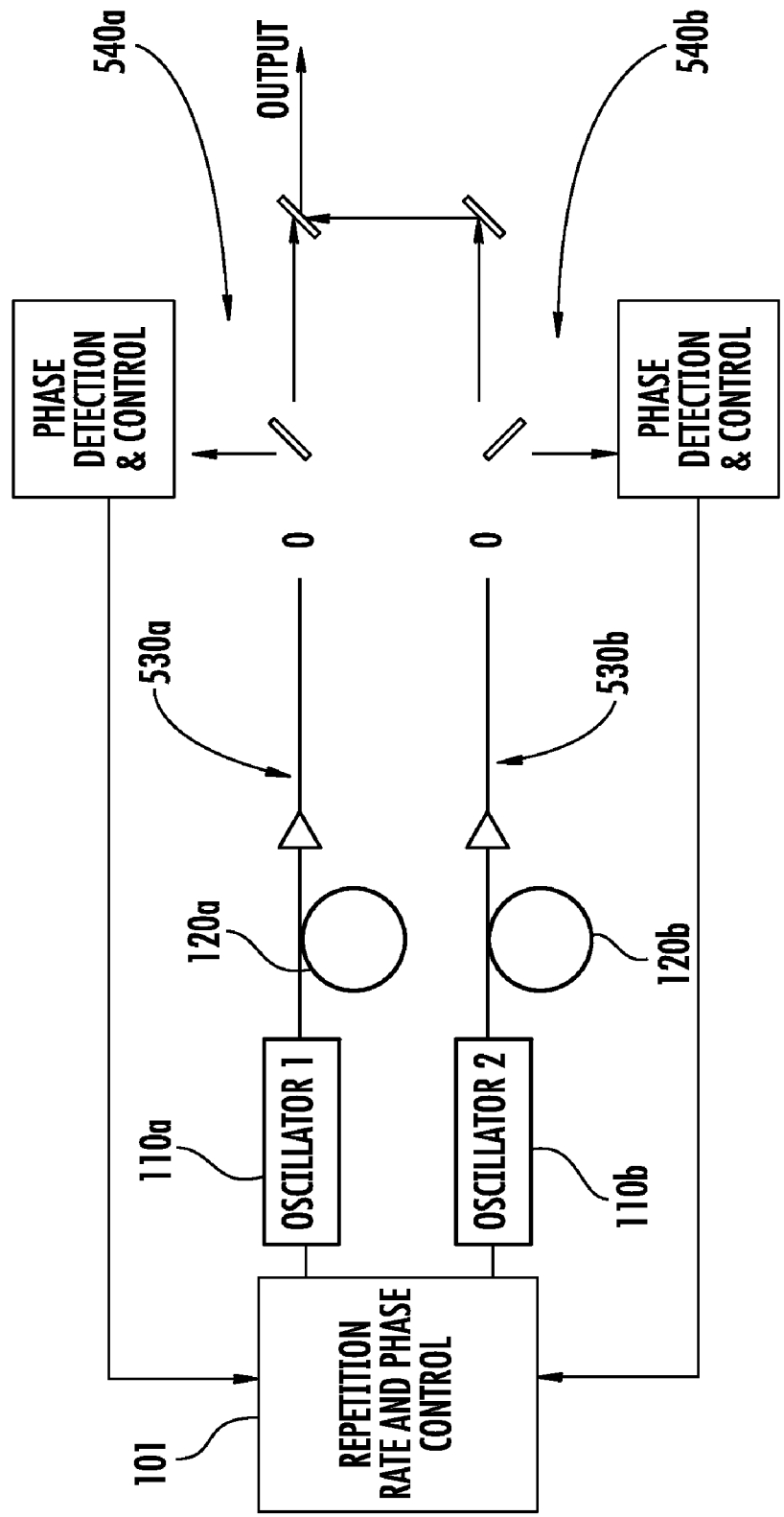
FIG. 5 is a schematic diagram of yet another CDSL based on carrier envelope offset frequency monitoring.

Another example of a CDSL is shown in FIG. 5. As described with respect to FIG. 1 the system also comprises a repetition rate controller 101, two oscillators 110a, 110b (oscillator 1 & oscillator 2) and amplifiers 120a, 120b. The system configuration is very similar to the system described with respect FIG. 1, but the DFG sections are eliminated. The output of the two oscillators propagates along two different propagation paths and is injected into two separate fiber optic amplifiers 520a,5200b. Preferably the amplifier and oscillator exhibit overlapping gain spectra. Preferably both oscillators emit chirp free pulses or pulses having nearly identical chirp. Preferably the dispersion along the two propagation paths is matched. Preferably the power of both oscillators can be adjusted over some range, for example by a variable attenuator. The output of the amplifiers is further directed through an optical isolator (not shown) before injection into two dispersion compensators and frequency conversion sections similar in design to the arms 125a-2, 125b-2 described with respect to FIG. 1. In this example the frequency conversion sections generate two preferably very broad supercontinuum spectra that can span an octave or more and can extend into the mid-IR when, for example, using highly nonlinear fluoride or chalcogenide waveguides. Several frequency conversion sections as well as intermediate amplifiers can be concatenated and frequency conversion stages based on PPLN waveguides or silicon waveguides can also be used.

In contrast to the system described with respect to FIG. 1, a portion of the output of the two generated supercontinua is diverted to two phase detection and control units 540a, 540b. Phase detection can for example be conveniently performed with an f–2f interferometer as discussed in U.S. Pat. No. 7,190,705 to Fermann et al. and Ser. No. 11/546,998 to Hartl et al. Such f–2f interferometers are therefore not further discussed here. The f–2f interferometer produces an RF beat signal corresponding to $f_{ceo}$ which is fed back to the oscillators for $f_{ceo}$ control via a feedback loop. The $f_{ceo}$ of both oscillators can be kept within an RF filter bandwidth by a frequency lock by feedback loops. For optimum precision of the feedback loop a phase locked loop can be implemented, but other feedback loops can also be implemented.

As discussed in U.S. Pat. No. 7,190,705 the temperature of an intra-cavity fiber grating inside a modelocked fiber oscillator can be used for carrier envelope phase control. Alternatively, as also discussed in '705, an external pressure can be applied to the fiber grating and pressure variations can be used for carrier envelope phase control.

In FIG. 6 a variety of techniques for carrier envelope phase control in a fiber oscillator are illustrated. In FIG. 6a a piece of intra-cavity fiber 601 is shown that contains a fiber Bragg grating for cavity dispersion control. In order to control the carrier-envelope offset frequency, the outside of the fiber grating is gold coated and a current is passed through the coating. The temperature of the grating can thus be controlled via resistive heating in the gold coating which in turn leads to a rapid modulation of the carrier-envelope offset frequency, which can then be stabilized via a feedback loop in conjunction with an f–2f interferometer.

Figure 6A:
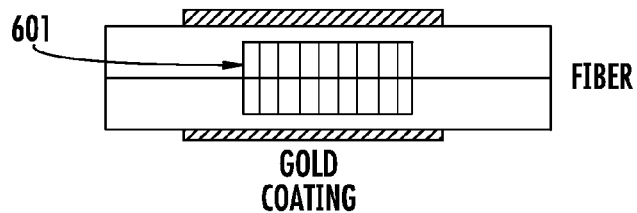
FIG. 6a is a schematic diagram of an intra-cavity assembly of a modelocked fiber oscillator for resistive heating of an intra-cavity fiber Bragg grating for carrier envelope offset frequency control.
Figure 6B:
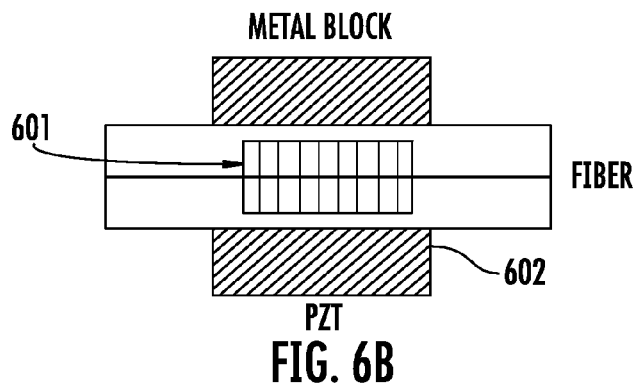
FIG. 6b is a schematic diagram of an intra-cavity assembly of a modelocked fiber oscillator for modulating the pressure applied to an intra-cavity fiber Bragg grating for carrier envelope offset frequency control.

In FIG. 6b a piezo-electric transducer (PZT) 602 applies pressure to one side of the fiber, which can also be modulated and used for intra-cavity carrier-envelope offset frequency control. The use of a PZT allows for faster feedback control compared to a resistive heater.

Figure 6C:
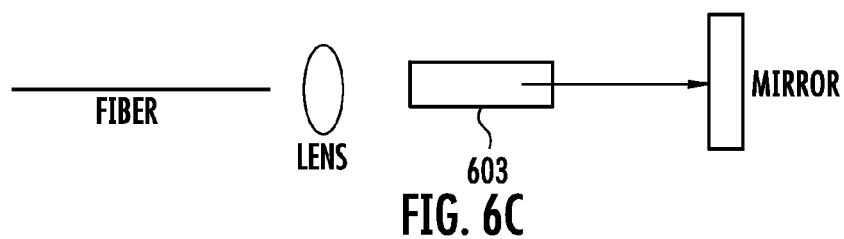
FIG. 6c is a schematic diagram of an assembly including an intra-cavity modulator as used for modulating the intra-cavity loss of a modelocked laser for carrier envelope offset frequency control.

Even faster carrier-envelope offset frequency control can be accomplished via an intra-cavity acousto-optic modulator (AOM) 603 as shown in FIG. 6c By changing the drive voltage to the AOM the loss inside the fiber oscillator can be rapidly modulated, which in turn leads to a modulation of the carrier-envelope offset frequency.

Figure 6D:
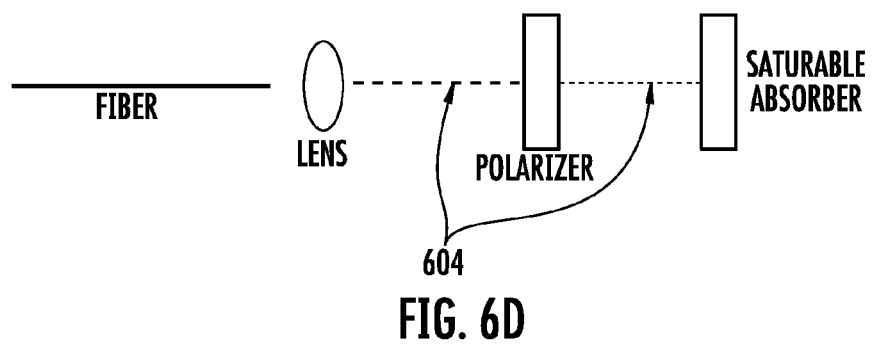
FIG. 6d is a schematic diagram of an intra-cavity assembly of a modelocked fiber oscillator for modulating the residual pump power impinging on an intra-cavity saturable absorber for carrier envelope offset frequency control.

In FIG. 6d the carrier-envelope offset frequency is controlled via a modulation of the residual pump power that is impinging on the intra-cavity saturable absorber. This is accomplished by inserting a polarizer in front of the saturable absorber and modulating the polarization of the pump light 604. The polarization of the pump light can be modulated in a variety of ways; essentially lossless and rapid polarization modulation is possible by passing the pump light through a length of polarization maintaining fiber which is coiled onto a PZT drum and exciting both axes of the polarization maintaining fiber equally with linearly polarized pump light.

Other means for carrier-envelope offset frequency control can also be implemented; for example the temperature of the intra-cavity saturable absorber can be modulated. Various combinations may also be implemented. Moreover, the feedback systems of FIG. 6 may also comprise multiple feedback loops for independent measurement and control of the carrier envelope offset frequency.

Figure 7:
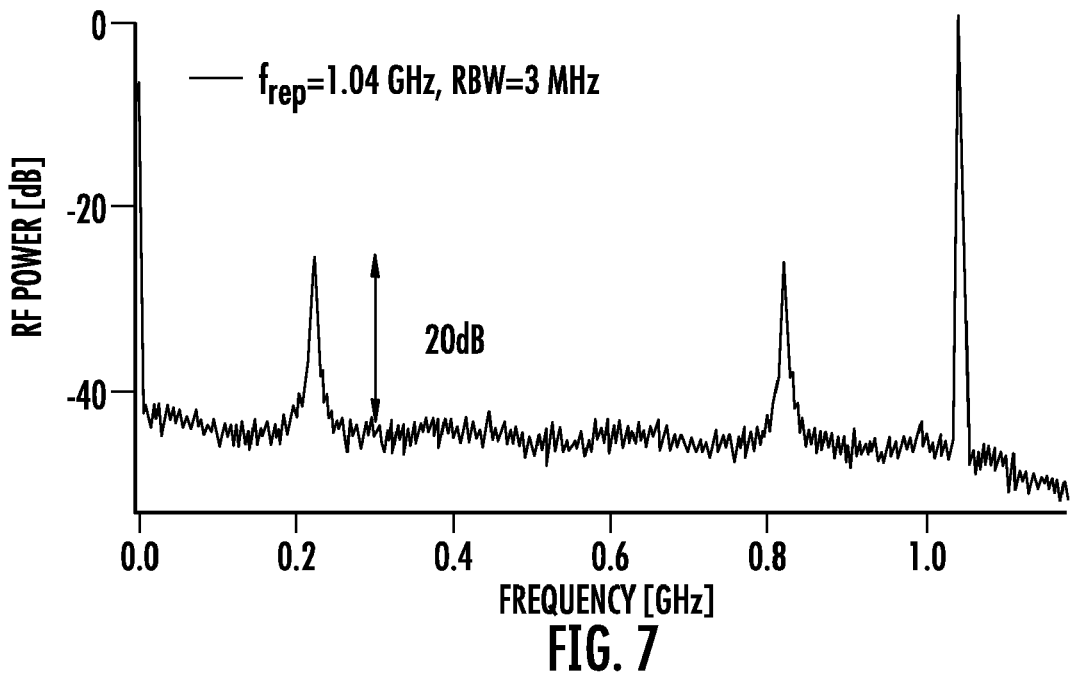
FIG. 7 is a plot of the RF spectrum of a carrier envelope offset frequency locked Yb fiber laser operating at a repetition rate of 1 GHz measured after a nonlinear f–2f interferometer.

In FIG. 7 the corresponding RF spectrum of a carrier envelope offset frequency locked Yb fiber laser operating at a repetition rate of 1.04 GHz measured after a nonlinear f–2f interferometer is shown. The RF spectrum shows a peak at 1 GHz corresponding to the repetition rate of the laser and two peaks at 210 and 830 MHz corresponding to the carrier envelope offset frequency.

Figure 8:
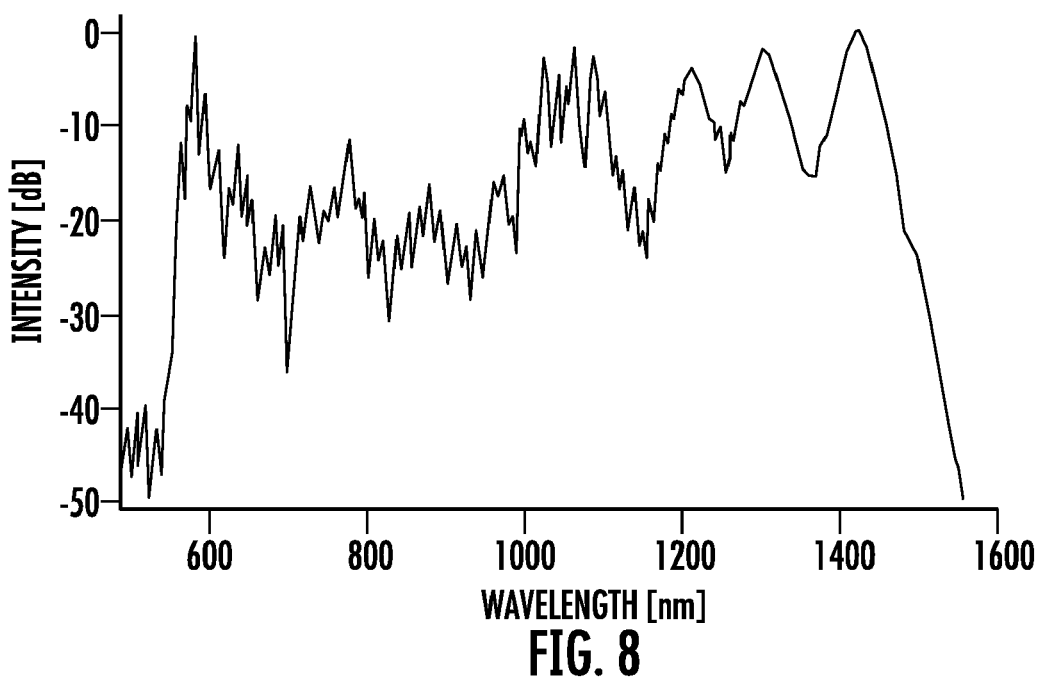
FIG. 8 is a plot of the spectral output of Yb fiber laser based coherent supercontinuum source operating at a repetition rate of 1 GHz.

FIG. 8 illustrates an example of a supercontinuum spectrum generated with a carrier-envelope phase locked Yb fiber laser operating at a repetition rate of 1 GHz. Here the supercontinuum was generated in a highly nonlinear optical fiber. The supercontinuum spectrum was recorded from one propagation path of the fiber system as shown in FIG. 5.

Rather than controlling $f_{ceo}$ with an f–2f interferometer, $f_{ceo}$ can also be controlled by referencing the frequency comb of a mode locked laser to the Fabry-Perot resonances of a passive cavity. This technique has some benefits: no octave spanning continuum generation is required and relatively small power levels which can be provided by a portion of the oscillator power are sufficient. This method is described in R. Jason Jones and Jean-Claude Diels "Stabilization of Femtosecond Lasers for Optical Frequency Metrology and Direct Optical to RadioSynthesis" PRL 86, p. 3288 (2001) and in R. Jason Jones et al. "Precision stabilization of femtosecond lasers to high-finesse optical cavities". Phys. Rev. A 69, 051803 (2004) which is hereby incorporated by reference in its entirety.

Figure 9:
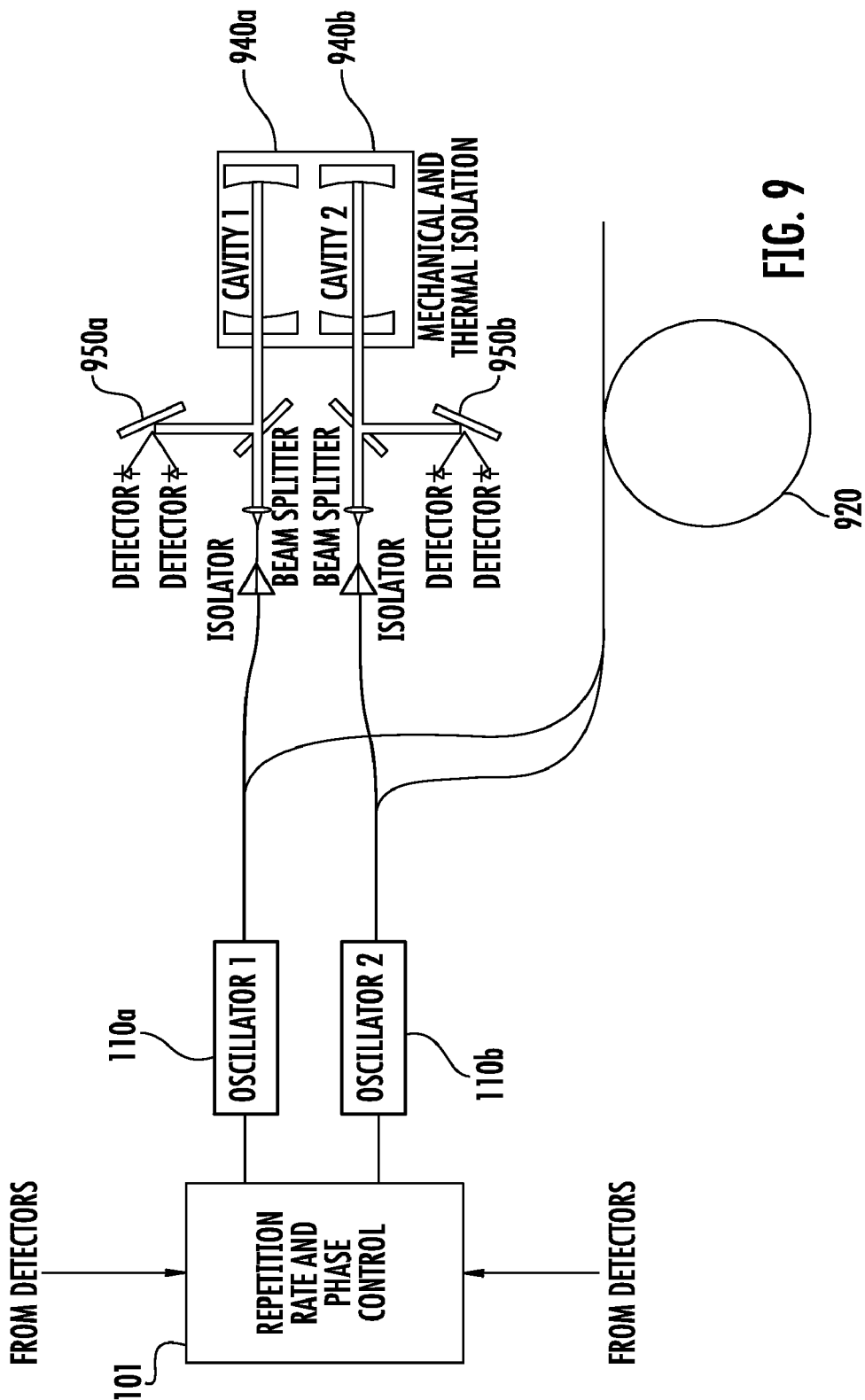
FIG. 9 is a schematic diagram of a dual scanning laser system which is locked to two external cavities for repetition rate and carrier phase control.

An embodiment utilizing external cavities is shown in FIG. 9. The oscillator 110a, 110b outputs are combined and coupled into a single propagation path, and amplified with fiber amplifier 920, as discussed above. A portion of each oscillator output is also directed to reference cavities 940a, 940b, and stabilized at two separated spectral regions to a reference cavity. In this example two reference cavities 940a, 940b with slightly different round trip times are shown. Both cavities are preferably in close thermal and mechanical contact for all thermally and mechanically induced fluctuations being in common mode. A configuration with one external cavity is also possible. When using only one cavity a birefringent element incorporated into the cavity provides for two different round-trip times along two polarization axes, where those two axes are in turn locked to each laser. Such an implementation is not separately shown.

Gratings 950a,950b direct two spectral regions of the oscillator output to two different detectors, which are then used to lock the two different oscillator comb teeth to two different resonances of the external cavities, which may be configured as passive cavities, or with feedback control. With the use of one or two external cavities all four degrees of freedom, namely $f_{ceo}$ of both lasers, as well as $f_{rep}$ and δ are referenced to the cavity modes. In a preferred embodiment a Pound Dreyer Hall scheme is used for locking the oscillators to the reference cavities. The Pound Dreyer Hall scheme requires the implementation of additional phase modulators (not shown) in the fiber pig-tails that transport the signal to the external cavities. Instead of separate phase modulators, phase modulation can also be implemented intra-cavity by for example modulating one cavity end mirror. The Pound Dreyer Hall scheme is well known in the state of the art for locking mode-locked fiber lasers to external cavities and is not further explained.

Figure 10:
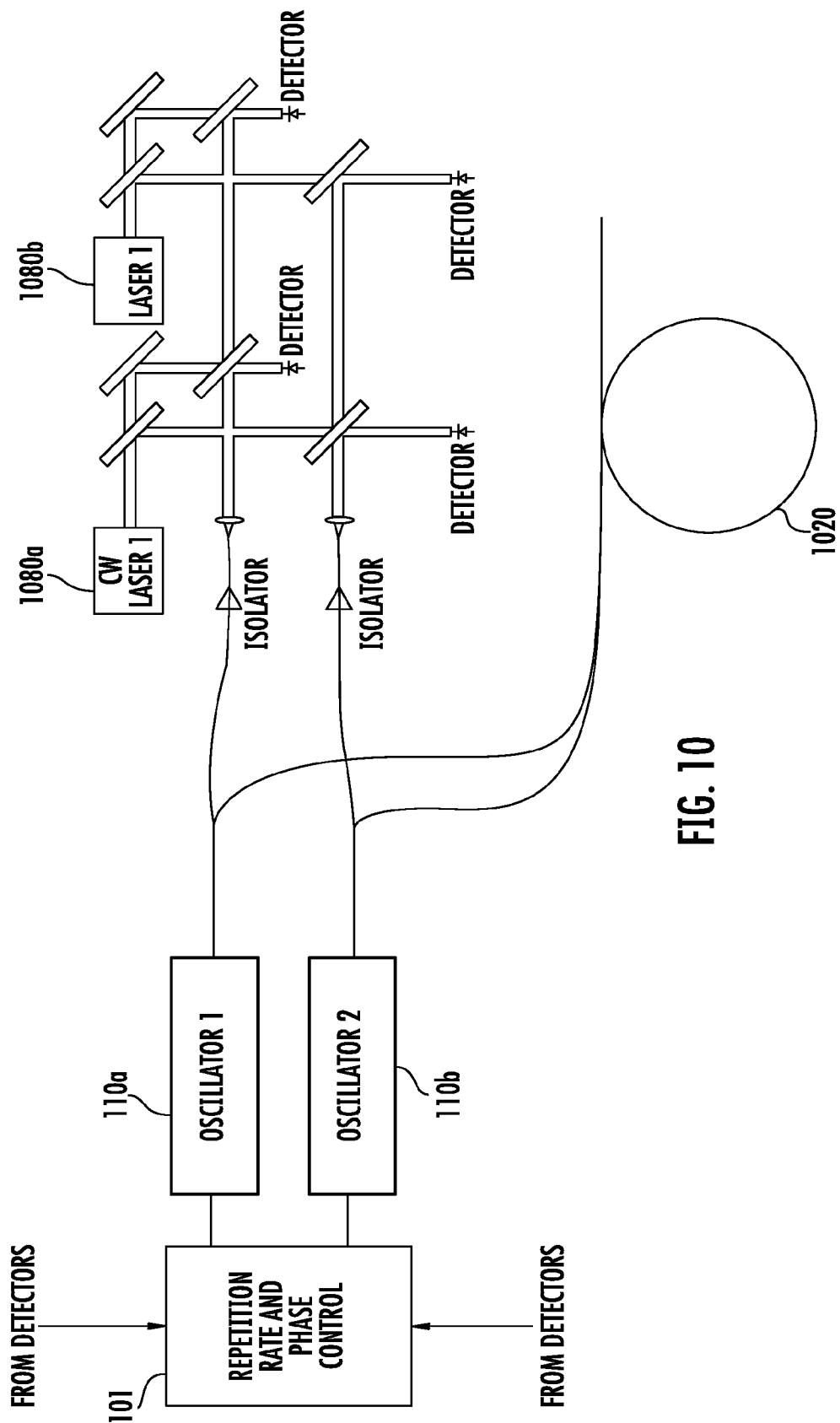
FIG. 10 is a schematic diagram of a dual scanning laser system which is locked to two narrow linewidth lasers for repetition rate and carrier phase control.

As an alternative to using passive cavities as stable references for repetition rate and carrier phase control of CDSLs cw reference lasers 1080a,1080b can be used as shown in FIG. 10. The oscillator 110a, 110b outputs are also combined and coupled into a single propagation path, and amplified with fiber amplifier 1020, as discussed above. Additionally, two stable, single frequency lasers are used for stablization. Such single frequency lasers are preferably based on semiconductor or fiber lasers and are commercially available. The frequencies of both single frequency lasers are different and are selected such that they both overlap with the spectra of the mode-locked lasers, preferably at the low and high frequency parts of the spectra. The frequency comb of each mode-locked laser can now be phase-locked at two comb teeth to the stable cw-lasers by feedback control to $f_{ceo}$ and $f_{rep}$ of both lasers, fixing two frequencies of each comb and therefore stabilizing $f_{ceo}$ and $f_{rep}$. When the stabilization is arranged such that for each mode-locked laser a different number of comb teeth are between the two fixed comb teeth, their repetition rates are different which is required for CDSL. An implementation of this stabilization method is described in I. Coddington, et al. "Coherent Multiheterodyne Spectroscopy Using Stabilized Optical Frequency Combs," Phys. Rev. Lett. 100, 13902 (2008), which is included by reference.

Figure 11:
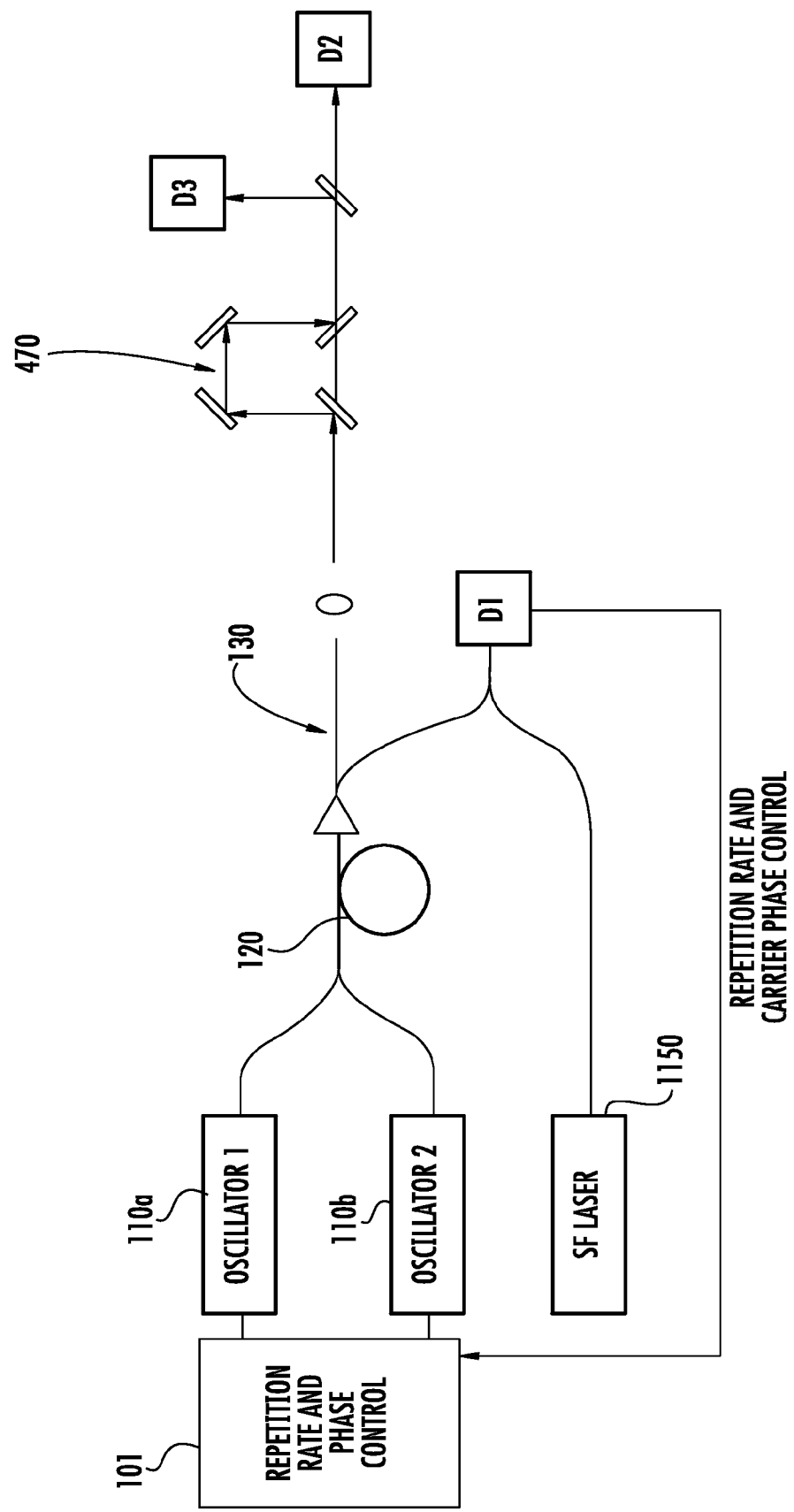
FIG. 11 is a schematic diagram of an ultra-compact dual scanning laser system which uses one external narrow linewidth laser for repetition rate and carrier phase control.

A compact and highly integrated configuration of a CDSL is shown in FIG. 11. The oscillator 110a, 110b outputs are combined and coupled into a single propagation path, and amplified with fiber amplifier 120, as discussed above. A portion of the amplified output is sampled and directed to detector D1. Alternatively, the output of the oscillators or the amplified outputs of the oscillators may be directed to two different detectors, such an implementation is not separately shown. A single frequency laser is used for repetition rate and carrier phase control. In this scheme one of the frequency teeth of oscillator 110a is locked to the single frequency laser via a phase-locked loop (PLL1) and one of the frequency teeth of oscillator 110b is locked to the single frequency laser via another phase-locked loop (PLL2). To ensure phase-locking the cavity length of each laser can be modulated. After phase locking of these two frequency teeth, the expression for the frequency spectra of the two oscillators can be written as $$mf_{rep} + f_{ceo1} = f_y + f_{b1} \tag{2}$$

$$n(f_{rep} + \delta) + f_{ceo2} = f_y + f_{b2}, \tag{3}$$

where $f_y$ is the frequency of the single-frequency laser and $f_{b1}$, $f_{b2}$ are the RF beat frequencies to which the frequency teeth of the two oscillators are locked; $\delta$ is the difference between the repetition rates of the lasers. $F_{rep}$ and $\delta$ can further be locked to two more RF reference signals by controlling, for example, the pump current to the lasers. We can further evaluate n and m by setting for example the laser conditions such that $mf_{rep}=f_y+f_{b1}$, where $f_y+f_{b1}$ is obtained from an external calibration using for example a wavemeter. The same procedure can be implemented to obtain n. In the following we assume for simplicity n=m. Taking the difference of eqs (2) and (3) we then obtain $$n\delta + \Delta f_{ceo} = \Delta f_b. \tag{4}$$

Since $\Delta f_b$ and $\delta$ are known and n, m can be a obtained using the calibration procedure described above, from eqs. (2) or (3), we can evaluate $\Delta f_{ceo}$ to great precision.

It can then be easily shown that for $\Delta f_{ceo} \neq 0$ the frequency grid in the RF domain is frequency shifted compared to eq. (1) and the relation between optical $f_{opt}$ and RF frequencies $f_{rf}$ is modified as $$f_{ops} = (f_{rf} - \Delta f_{ceo})f_{rep}/\delta + f_{ceo1} \approx (f_{rf} - \Delta f_{ceo})f_{rep}/\delta, \tag{5}$$

Here we can simplify eq. (5) since $f_{ceo} \ll f_{opt}$. In this example $\Delta f_{ceo}$ stabilized rather than the individual carrier envelope offset frequencies in order to obtain an accurate RF frequency grid for the measurement of optical frequencies.

To obtain the best long-term precision for frequency measurements with a CDSL system, both oscillators are preferably packaged in close proximity in order to equalize any thermal fluctuations of laser parameters between the two lasers. Also, the single frequency reference laser is also preferably packaged with good thermal control.

Additionally, the system can be set up with amplifiers and nonlinear frequency conversion sections for increased spectral coverage. A temporal delay line 470 can be inserted in front of the detectors D2,D3 to detect pulse interference without temporal pulse overlap in the nonlinear stages. Also, two detectors D2, D3 can be used, where one detector is used for detection of a reference spectrum and the other is used to determine the absorption characteristics of a sample.

The system of FIG. 11 is beneficial for commercial applications because it can operate with a few components and a high level of optical integration.

The embodiments described above may be combined in various ways to produce alternative implementations. Many possibilities exist, and various modifications may be made based on specific applications. For example, a non-linear frequency conversion section may be configured with at least one non-linear fiber amplifier to broaden a spectrum.

Referring back again to FIG. 5, a phase control unit can also be replaced with a phase monitor unit. For example a phase monitor unit can comprise a fiber optic tap splitter (inserted in front of the amplifier) which diverts some of the oscillator light, and selects two narrow spectral lines from the oscillator spectra to monitor the carrier envelope offset frequency and repetition rate evolution. The carrier envelope offset frequency evolution can also be monitored after the amplifier or the first frequency conversion stage, but usage of the oscillator signal provides for the lowest noise. Such phase monitor units were discussed in Giaccari et al. and are not separately described here. As an alternative to such a phase monitor unit also two f–2f interferometers can be used which monitor the carrier envelope offset frequency of the two oscillators. As discussed with respect to FIG. 3 the output of the CDSL can be passed through an optical sample and can also be directed to a detector, where beat frequencies in the RF domain are observable. Due to scaling of the optical frequencies to the RF frequencies with a scaling factor $f_{rep}/\delta$ in CDSLs, we can interpret the function of the scanning dual laser system as providing a frequency grid in the RF domain for scaling RF to optical frequencies, i.e. each optical frequency is mapped onto a RF frequency. When locking the carrier envelope offset frequencies of the two lasers to different values eq. (5) can be used to obtain an accurate RF frequency grid for the measurement of optical frequencies.

More complex modifications of the RF frequency grid and the relation between optical and RF frequencies are obtained for small continuous variations of $\Delta f_{ceo}$ as well as $\delta$. By the implementation of a phase monitor unit the appropriate corrections of the RF frequency grid can be calculated in order to obtain an accurate conversion of RF to optical frequencies. Such corrections to the RF frequency grid were discussed by Giaccari and are not further described here. Similar corrections can also be applied when monitoring $\Delta f_{ceo}$ with an f–2f interferometer. Since the f–2f interferometer allows a direct reading of $f_{ceo}$ for of each oscillator using RF techniques, $\Delta f_{ceo}$ can be easily computed and the optical frequencies can be calculated using equation (5).

The imaging arrangement as discussed with respect to FIG. 3 can also be extended to the THz range. As discussed by Yasui et al., in Appl. Phys. Lett., vol. 88, pp. 211104-1 to 3 (2006) a THz comb is generated by a photo-conductive emitter excited by a femtosecond laser. The same applies also when generating THz pulses via optical rectification in an electro-optic crystal. Moreover, the frequency comb in the THz frequency range comprises pure harmonics of the laser repetition rate. Thus two slightly offset THz frequency combs can be generated by directing the output of a CDSL system onto an electro-optic crystal or a photo-conductive emitter. A system for generating THz frequency combs and imaging in the THz spectral range can thus be constructed similar to the implementation shown in FIGS. 3 and 5, where the frequency conversion section and the phase control sections are omitted and the nonlinear frequency conversion section is replaced with an electro-optic crystal such as for example GaP, GaSe, periodically poled LiNbO$_3$, optically patterned GaAs or a photo-conductive antenna. Appropriate THz optics can then be used for imaging the THz radiation onto a sample, which is conveniently placed on a movable stage for optical scanning. In various embodiments the scanner may be omitted, in part because of the present limited availability of scanners suitable for use over the THz frequency range. An appropriate detector such as a photo-conductive antenna can then monitor the RF beat signal from which the THz spectrum can be inferred using an RF analysis of the detected photo-current in the detector as discussed by Yasui et al.

Thus the inventors have described CDSLs and some applications thereof, and various alternatives for implementation including highly integrated configurations.

In at least one embodiment a coherent dual scanning laser system (CDSL) includes two passively modelocked fiber oscillators. The oscillators are configured to operate at slightly different repetition rates, such that a difference $\delta f_r$ in repetition rates is small compared to the values $f_{r1}$ and $f_{r2}$ of the repetition rates of the oscillators. The CDSL system also includes a non-linear frequency conversion section optically connected to each oscillator. The section includes a non-linear optical element generating a frequency converted spectral output having a spectral bandwidth and a frequency comb comprising harmonics of the oscillator repetition rates.

In various embodiments:

a frequency conversion section includes an output section that receives and combines multiple input frequencies and generates a spectral output at a difference frequency thereof, and the system includes an intermediate non-linear frequency conversion section between at least one oscillator and the output section, the intermediate section generating a broadband spectrum having a bandwidth substantially greater than an oscillator spectrum.

a CDSL is arranged in a measurement system that utilizes spectral information, and a spectral output is utilized to probe a physical property of a test sample with spectral components within the spectral bandwidth.

a CDSL is arranged in an imaging system for one or more of optical imaging, microscopy, micro-spectroscopy and/or THz imaging.

a CDSL based measurement system may include an element for optical scanning.

a phase-locked loop controls the difference in repetition rates between the oscillators.

an RF spectrum analyzer generates an output at RF frequencies related to the optical frequencies with a conversion factor $(f_{r1}+f_{r2})/2\delta f_r$.

mode locked fiber oscillators comprise an Nd, Yb, Tm or Er fiber oscillator.

at least one fiber amplifier is included for amplifying one or more oscillator outputs.

an integrated, all-fiber, dispersion compensator and non-linear frequency conversion section is included, the integrated section comprising one or more of a highly nonlinear fiber, a photonic crystal fiber, a dispersion compensating fiber and/or a fiber having a central air-hole.

a system includes a bulk optical element for dispersion compensation, including at least one of a grating pair, prism pair and/or grism pair, wherein dispersion compensation comprises pulse compression.

a nonlinear frequency conversion section comprises a difference frequency generator.

a non-linear frequency section includes a supercontinuum generator disposed downstream of at least one oscillator.

a mode locked fiber oscillator generates pulses at a repetition rate greater than about 250 MHz.

In at least one embodiment a coherent dual scanning laser system includes two passively modelocked fiber oscillators. The oscillators are configured to operate at slightly different repetition rates, such that a difference $\delta f_r$ in repetition rates is small compared to the values $f_{r1}$ and $f_{r2}$ of the repetition rates of two oscillators. The CDSL also includes a non-linear frequency conversion section optically connected to each oscillator, the section comprising a non-linear optical element generating a frequency converted spectral output having a spectral bandwidth and a frequency comb structure with a frequency separation equivalent to the oscillator repetition rates. The nonlinear frequency conversion section produces a spectral output substantially broader than the spectral output from each oscillator.

In various embodiments:

a means for monitoring the difference in the carrier envelope offset frequencies of the two lasers is included, wherein information generated by the monitoring means provides a 1:1 correspondence between RF frequencies and optical frequencies.

a correspondence is represented with a 1:1 mapping of said RF frequencies to optical frequencies.

an f–2f interferometer is included for carrier envelope offset frequency control of each laser.

a feedback system is included for stabilizing the difference in the carrier envelope offset frequencies of the two oscillators.

carrier envelope offset frequency information generated by the feedback system is used to generate a frequency grid in the RF domain that has a one to one correspondence to a frequency grid in the optical domain.

a feedback system includes a single-frequency reference laser.

two reference cavities are utilized for carrier envelope offset frequency control of each oscillator.

one reference cavity is utilized for carrier envelope offset frequency control of each oscillator.

two single-frequency reference lasers are utilized for carrier envelope offset frequency control of each oscillator.

a non-linear frequency conversion section comprises a highly non-linear fiber.

a ratio of a repetition rate to the difference in repetition rates is at least about $10^6$, and may be in the range of about $10^6$ to about $10^9$.

The repetition rates $f_{r1}$, $f_{r2}$, and ratio of a repetition rate to the difference in repetition rates are sufficiently high to convert an RF frequency to an optical frequency.

At least one embodiment includes a system for imaging in the THz spectral range. The imaging system includes a coherent dual scanning laser system (CDSL) having two passively modelocked fiber oscillators. The modelocked oscillators are configured to operate at slightly different repetition rates, such that a difference $\delta f_r$ in repetition rates is small compared to the values $f_{r1}$ and $f_{r2}$ of the repetition rates of the oscillators. The system includes a material emitting THz radiation in response to an output of said CDSL, and a detector responsive to said THz radiation.

In at least one embodiment a coherent dual scanning laser system includes two passively modelocked oscillators generating at least two trains of short optical pulses. The oscillators are configured to operate at slightly different repetition rates, such that a difference in repetition rates $\delta f_r$ is small compared to the values $f_{r1}$ and $f_{r2}$ of the repetition rates of the oscillators. The system includes a beam combiner for spatially combining trains of short optical pulses to propagate along a common optical path downstream of the beam combiner. A non-linear optical element is included for spectrally broadening at least one train of said short optical pulses propagating along the common optical path. A dual arm interferometer is configured with different arm lengths so as to detect interference between pulse trains when the pulses are not temporally overlapping in time prior to entering the interferometer.

In various embodiments an arm length difference corresponds to approximately half the cavity round trip time of said oscillators.

In at least one embodiment a coherent dual scanning laser system includes two passively modelocked fiber oscillators generating two separate trains of short optical pulses. The oscillators are adjusted to operate at slightly different repetition rates, such that a difference $\delta f_r$ in repetition rates is small compared to the values $f_{r1}$ and $f_{r2}$ of the repetition rates of the oscillators. A feedback system stabilizes the difference in the carrier envelope offset frequencies of the two oscillators, and the feedback system includes a single-frequency laser. A beam combiner spatially combines trains of short optical pulses to propagate along a common optical path downstream of the beam combiner. The system includes a non-linear optical element for spectrally broadening at least one train of short optical pulses propagating along a common optical path. A dual arm interferometer is configured with different arm lengths so as to detect interference between pulse trains when the pulses are not temporally overlapping in time prior to entering the interferometer.

Thus, while only certain embodiments have been specifically described herein, it will be apparent that numerous modifications may be made thereto without departing from the spirit and scope of the invention. Further, acronyms are used merely to enhance the readability of the specification and claims. It should be noted that these acronyms are not intended to lessen the generality of the terms used and they should not be construed to restrict the scope of the claims to the embodiments described therein.

What is claimed is:

1. A system for imaging in the THz spectral range comprising:
    a coherent dual scanning laser system (CDSL) comprising two passively modelocked fiber oscillators, said modelocked oscillators configured to operate at slightly different repetition rates, such that a difference δfr in repetition rates is small compared to the values fr1 and fr2 of the repetition rates of said oscillators;
    a feedback system for stabilizing the difference in the repetition rates of the two oscillators, wherein information generated by said feedback system is used to generate a frequency grid in the RF domain that has a 1:1 correspondence to a frequency grid in the THz domain, and allowing an RF frequency to be scale to a THz frequency;
    a material emitting THz radiation in response to an output of said CDSL; and
    a detector responsive to said THz radiation.

2. A system for imaging in the THz spectral range comprising:
    a coherent dual scanning laser system (CDSL) comprising two passively modelocked fiber oscillators, said modelocked oscillators configured to operate at slightly different repetition rates, such that a difference δfr in repetition rates is small compared to the values fr1 and fr2 of the repetition rates of said oscillators;
    a monitoring system for monitoring the difference in the repetition rates of the two oscillators, wherein information generated by said monitoring system is used to generate a frequency grid in the RF domain that has a 1:1 correspondence to a frequency grid in the THz domain, and allowing an RF frequency to be scale to a THz frequency;
    a material emitting THz radiation in response to an output of said CDSL; and
    a detector responsive to said THz radiation.

* * * * *